(12) United States Patent
Kim et al.

(10) Patent No.: US 9,452,192 B2
(45) Date of Patent: Sep. 27, 2016

(54) COMPOSITION FOR PREVENTING OR IMPROVING METABOLIC SYNDROME COMPRISING TEA PLANT LEAF, FLOWER AND SEED EXTRACT

(71) Applicant: AMOREPACIFIC CORPORATION, Seoul (KR)

(72) Inventors: Su Kyung Kim, Yongin-si (KR); Hyun Jung Shin, Yongin-si (KR); Chan Su Rha, Yongin-si (KR); Seung Hun Kim, Yongin-si (KR); Bum Jin Lee, Yongin-si (KR); Young Kyung Kim, Yongin-si (KR); Dae Bang Seo, Yongin-si (KR); Wan Gi Kim, Yongin-si (KR); Jin Oh Chung, Yongin-si (KR); Sang Jun Lee, Yongin-si (KR)

(73) Assignee: AMOREPACIFIC CORPORATION (KR)

( * ) Notice: Subject to any disclaimer, the term of this patent is extended or adjusted under 35 U.S.C. 154(b) by 80 days.

(21) Appl. No.: 13/722,676

(22) Filed: Dec. 20, 2012

(65) Prior Publication Data

US 2013/0171277 A1 Jul. 4, 2013

(30) Foreign Application Priority Data

Dec. 30, 2011 (KR) .................. 10-2011-0147304

(51) Int. Cl.
*A61K 36/82* (2006.01)

(52) U.S. Cl.
CPC .................. *A61K 36/82* (2013.01)

(58) Field of Classification Search
CPC ..................................... A61K 36/82
USPC .................. 424/729, 774, 776, 778
See application file for complete search history.

(56) References Cited

U.S. PATENT DOCUMENTS

2004/0097432 A1* 5/2004 Roh-Schmidt et al. ......... 514/27
2008/0268075 A1* 10/2008 Samuel et al. ................ 424/729

FOREIGN PATENT DOCUMENTS

| CN | 101392015 A | * | 2/2009 |
| JP | 2011051950 A | * | 3/2011 |
| KR | 10-2006-008570 A | * | 1/2006 |
| KR | 1020080090805 A | | 9/2008 |

OTHER PUBLICATIONS

Mayo Clinic: Metabolic Syndrome (http://www.mayoclinic.org/diseases-conditions/metabolic-syndrome/basics/definition/con-20027243?p=1)—accessed Jul. 2014.*
NIH: What is Metabolic Syndrome? (http://www.nhlbi.nih.gov/health/health-topics/topics/ms/)—accessed Jul. 2014.*

* cited by examiner

*Primary Examiner* — Susan Hoffman
(74) *Attorney, Agent, or Firm* — Cantor Colburn LLP

(57) ABSTRACT

Disclosed is a composition for preventing or improving metabolic syndrome, including a tea plant leaf extract, a tea plant flower extract and a tea plant seed extract as active ingredients.

4 Claims, 6 Drawing Sheets

FIG.4
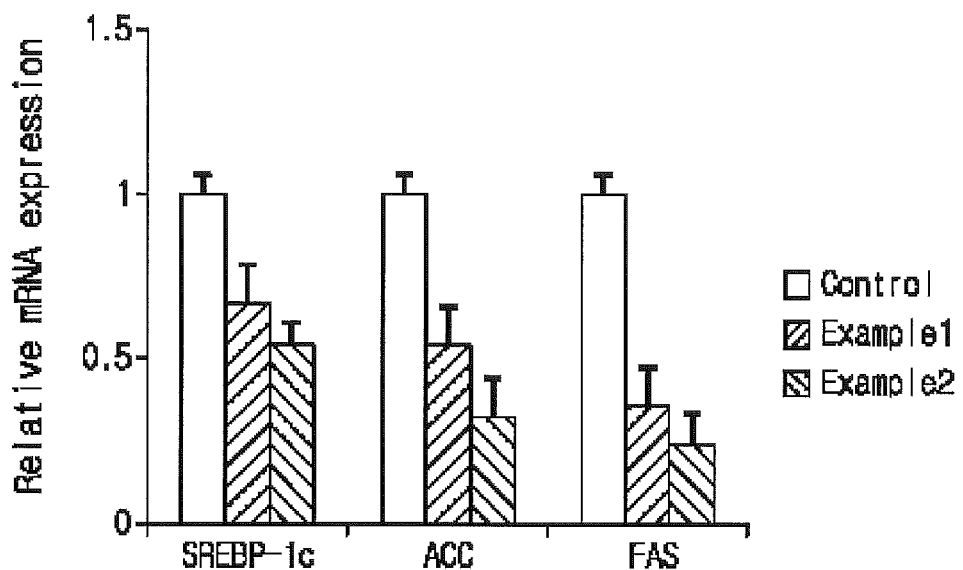
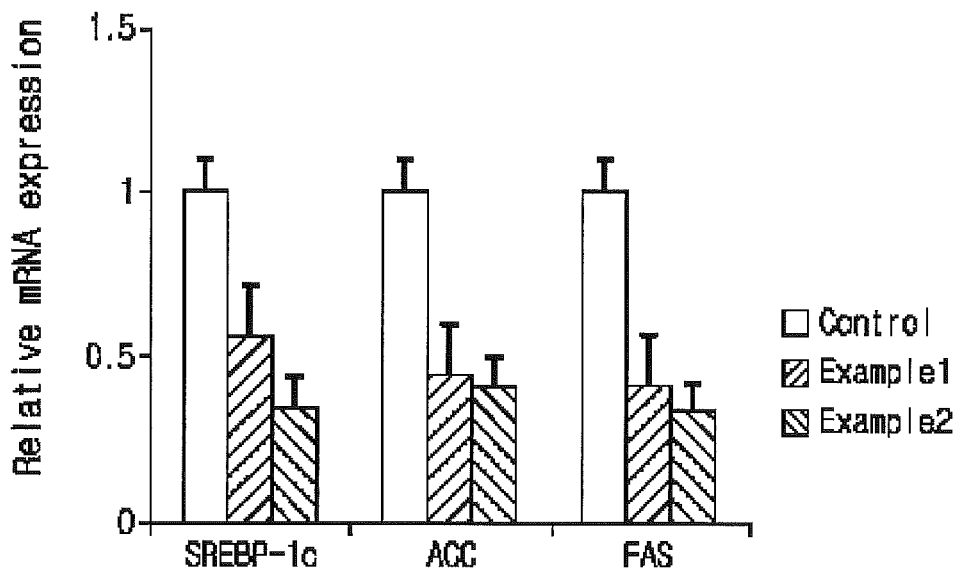

COMPOSITION FOR PREVENTING OR IMPROVING METABOLIC SYNDROME COMPRISING TEA PLANT LEAF, FLOWER AND SEED EXTRACT

CROSS-REFERENCE TO RELATED APPLICATION

This application claims priority to Korean Patent Application No. 10-2011-0147304, filed on Dec. 30, 2012, and all the benefits accruing there from under 35 U.S.C. §119, the contents of which in its entirety are herein incorporated by reference.

BACKGROUND

1. Field

The present disclosure relates to a composition for preventing or improving metabolic syndrome, comprising a tea plant leaf extract, a tea plant flower extract and a tea plant seed extract.

2. Description of the Related Art

In recent years, obesity is increasing because of increased intake of nutrients such as fats, simple sugars, etc. due to westernized eating habits and lack of exercise, leading to accumulation of excess energy in the body. The accumulated energy is stored in the form of triglycerides in adipose tissues. If the excess energy to be stored exceeds the capacity of the adipose tissues, the triglycerides may be accumulated in other tissues such as muscle, liver, etc., leading to lipid dysregulation and lipotoxicity. The fats stored in the tissues are broken down into free fatty acids through lipolysis. The free fatty acids are known to suppress the insulin signal transduction pathway through signaling via JNK, PKC, etc. The suppressed insulin signal transduction pathway inevitably leads to insulin resistance, resulting in increased insulin secretion to compensate for the altered function of insulin. The excessively secreted insulin increases salts, water and fats in the body and stimulates the sympathetic nerve, leading to increased heart rate and constriction of blood vessels, thereby increasing the risk of obesity, high blood sugar, high blood pressure, dyslipidemia (low HDL cholesterol and high triglyceride levels) and metabolic syndrome.

SUMMARY

The present disclosure is directed to providing a composition for preventing or improving metabolic syndrome.

In one aspect, there is provided a composition for preventing or improving metabolic syndrome, including a tea plant leaf extract, a tea plant flower extract and a tea plant seed extract as active ingredients.

In another aspect, there is provided a pharmaceutical or food composition for preventing or improving metabolic syndrome, including a tea plant leaf extract, a tea plant flower extract and a tea plant seed extract as active ingredients.

The composition comprising a tea plant leaf extract, a tea plant flower extract and a tea plant seed extract as active ingredients according to the present disclosure exhibits a synergic effect of activating AMPK, inhibiting fatty acid synthesis, facilitating fatty acid oxidation and promoting glucose uptake, and provides better effect of preventing and improving metabolic syndrome as compared to a composition comprising only the tea leaf extract.

BRIEF DESCRIPTION OF THE DRAWINGS

The above and other aspects, features and advantages of the disclosed exemplary embodiments will be more apparent from the following detailed description taken in conjunction with the accompanying drawings in which:

FIG. 4 shows decreased expression of fatty acid biosynthesis-related genes in adipocytes and hepatocytes treated with a mixture of a tea plant leaf extract, a tea plant flower extract and a tea plant seed extract;

DETAILED DESCRIPTION

Figure 1:
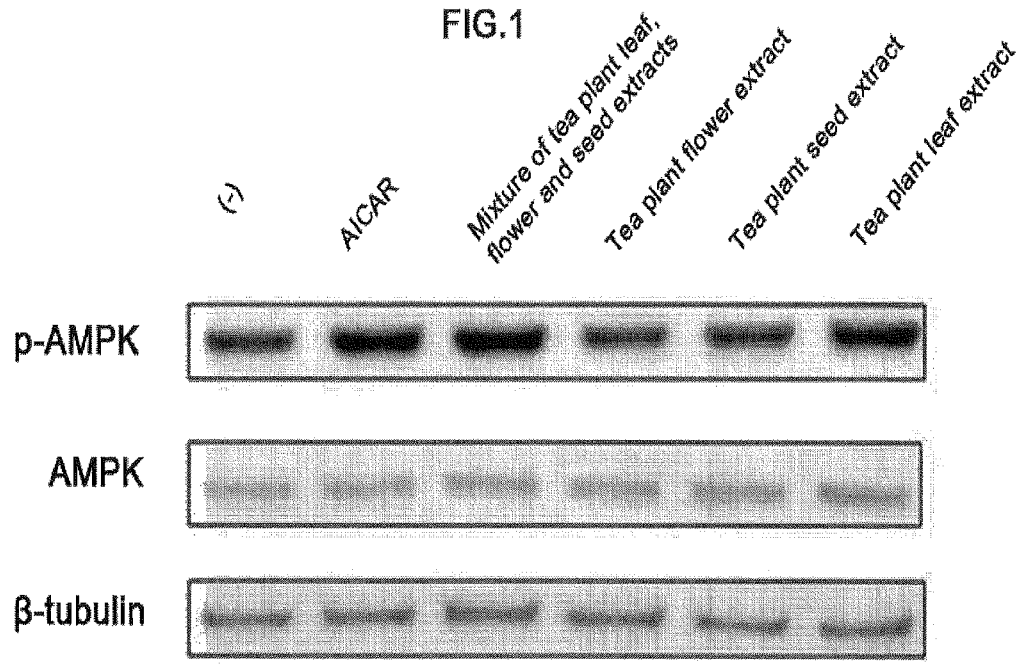
FIG. 1 shows change in AMPK activity after treating hepatocytes with a tea plant leaf extract, a tea plant flower extract, a tea plant seed extract or a mixture of the extracts.

Exemplary embodiments now will be described more fully hereinafter with reference to the accompanying drawings, in which exemplary embodiments are shown.

As used herein, the term "extract" includes any substance extracted from a natural product, regardless of extraction method, extraction solvent, extracted ingredients or type of the extract.

AMPK (5' AMP-activated protein kinase) is a protein kinase that plays a major role in energy homeostasis such as glucose transport, fatty acid synthesis and cholesterol biosynthesis. The activity of AMPK is altered in response to the energy state (the ratio of ATP to AMP) changed by exercise, stress or nutrition. In particular, the expression of AMPK is increased in an energy-deficient state to suppress synthesis of fat and glycogen in adipocytes, hepatocytes and myocytes and promote degradation of stored fat to supply required energy. That is to say, activation of AMPK leads to increased glucose uptake in muscles as well as activation of the fat synthesis-related enzyme acetyl-CoA carboxylase (ACC) and decreased expression of sterol regulatory element-binding protein-1 (SREBP-1) in the liver. In addition to the inhibition of glucose synthesis, the enzymes involved in fat synthesis are deactivated, resulting in increased oxidation of fatty acids, suppressed synthesis of very-low-density lipoproteins (VLDL) and increased insulin sensitivity of metabolic tissues. Accordingly, a substance that can regulate the activity of AMPK is expected to be capable of preventing or improving metabolic syndrome that can lead to obesity, hyperlipidemia, hypertension, type 2 diabetes or cardiovascular diseases such as arteriosclerosis, myocardial infarction or angina by enhancing metabolic activity.

As used herein, the term "tea plant" refers to *Camellia sinensis* in the family Theaceae. From long ago, the extract of tea plant leaf is known to be effective in reducing body weight and body fat. However, the use of tea plant has been limited to tea plant leaves and the flower or seed of tea plant has been discarded due to lack of studies thereabout. The inventors of the present disclosure have discovered a superior effect of tea plant flower and seed extracts and invented a composition comprising a mixture of a tea plant leaf extract, a tea plant flower extract and a tea plant seed extract, which has an excellent effect of preventing and improving metabolic syndrome as compared to the tea plant leaf extract alone.

In an aspect, the present disclosure provides a composition for preventing or improving metabolic syndrome, comprising a tea plant leaf extract, a tea plant flower extract and a tea plant seed extract as active ingredients. A mixture of a tea plant leaf extract, a tea plant flower extract and a tea plant seed extract activates AMPK, especially in adipocytes, hepatocytes and myocytes involved in metabolism. The mixture may inhibit fatty acid synthesis and facilitate fatty acid oxidation at the same time by decreasing expression of the fatty acid synthesis-related genes SREBP-1c (sterol regulatory element-binding protein-1c), ACC (acetyl-CoA carboxylase) and FAS (fatty acid synthase) and increasing expression of the fatty acid oxidation-related genes ACO (acyl-CoA oxidase), CPT1 (carnitine palmitoyl transferase 1) and mCAD (medium-chain acyl-CoA dehydrogenase). This means that the mixture can increase consumption of fat and inhibit accumulation of surplus fat in the body by facilitating fat metabolism. In addition, the mixture can increase insulin sensitivity by promoting glucose uptake. Accordingly, the composition comprising a tea plant leaf extract, a tea plant flower extract and a tea plant seed extract as active ingredients has a superior effect of preventing or improving metabolic syndrome.

To sustain life, a living organism takes in nutrients and digests and stores them as source of energy. Also, it breaks them down to perform various life activities using energy released therefrom. These actions are collectively called "metabolism". As used herein, the term "metabolic syndrome" refers to a condition in which a living organism including human or animal cannot perform the metabolism normally. In an exemplary embodiment of the present disclosure, the metabolic syndrome comprises glucose metabolic syndrome or lipid metabolic syndrome caused by disorder of glucose or lipid metabolism, respectively. In another exemplary embodiment of the present disclosure, the metabolic syndrome comprises symptoms or diseases caused by disorder of glucose or lipid metabolism, specifically symptoms or diseases caused by excessive fat accumulation due to fatty acid metabolism disorder. For example, it includes one or more of obesity, hyperlipidemia, hypertension, type 2 diabetes and cardiovascular diseases such as arteriosclerosis, myocardial infarction or angina, but is not limited thereto.

In an exemplary embodiment of the present disclosure, the mixture of a tea plant leaf extract, a tea plant flower extract and a tea plant seed extract may be prepared by extracting the leaf, flower and seed of tea plant using hot water or an organic solvent and mixing thus obtained extracts. The organic solvent comprise one or more selected from a group consisting of alcohol, acetone, ether, ethyl acetate, diethyl ether, ethyl methyl ketone and chloroform, but is not limited thereto. The alcohol comprises a $C_1$-$C_5$ low alcohol and the $C_1$-$C_5$ low alcohol comprise one or more selected from a group consisting of methanol, ethanol, isopropyl alcohol, n-propyl alcohol, n-butanol and isobutanol, but is not limited thereto.

In an exemplary embodiment of the present disclosure, the composition comprising a tea plant leaf extract, a tea plant flower extract and a tea plant seed extract may be prepared by: preparing a tea plant leaf extract; preparing a tea plant flower extract; preparing a tea plant seed extract; and mixing the tea plant leaf extract, the tea plant flower extract and the tea plant seed extract. In another exemplary embodiment of the present disclosure, the composition comprising a tea plant leaf extract, a tea plant flower extract and a tea plant seed extract may be prepared by: mixing a tea plant leaf, a tea plant flower and a tea plant seed; and preparing an extract of the mixture.

A composition comprising a tea plant leaf extract, a tea plant flower extract and a tea plant seed extract according to an exemplary embodiment of the present disclosure may comprise the tea plant leaf extract and the tea plant flower extract plus the tea plant seed extract at a weight ratio of 4-12:0.2-8, specifically 5-10:0.5-6, more specifically 6-9:0.5-4, further more specifically 6-9:2-4. Within the above-described weight ratio range, a better effect of preventing or improving metabolic syndrome may be achieved as the content of the tea plant flower extract plus the tea plant seed extract is higher based on the weight of the tea plant leaf extract. And, within the above-described weight ratio range, the tea plant flower extract and the tea plant seed extract may be included at a weight ratio of 1-2:1-2, A composition comprising a tea plant leaf extract, a tea plant flower extract and a tea plant seed extract according to another exemplary embodiment of the present disclosure may comprise the tea plant leaf extract, the tea plant flower extract and the tea plant seed extract at a weight ratio of 4-12:0.3-4:0.3-4, specifically 5-10:0.3-3:0.3-3, more specifically 6-9:0.5-2:0.5-2, further more specifically 6-9:1-2:1-2. The above-described weight ratio range is appropriate to achieve the effect desired by the present disclosure while ensuring both stability and safety of the composition. Also, this range is appropriate in terms of cost effectiveness.

A composition according to an exemplary embodiment of the present disclosure may comprise 1-80 wt %, specifically 20-70 wt %, more specifically 30-60 wt % of the tea plant leaf extract, the tea plant flower extract and the tea plant seed extract based on the total weight of the composition. This range is appropriate to achieve the effect desired by the present disclosure while ensuring both stability and safety of the composition. Also, this range is appropriate in terms of cost effectiveness. Specifically, if the content of the tea plant leaf extract, the tea plant flower extract and the tea plant seed extract is less than 1 wt %, a sufficient effect of improving metabolic syndrome may not be achieved. And, if it exceeds 80 wt %, safety and stability of the composition may be insufficient.

In another aspect, the present disclosure provides a pharmaceutical composition comprising a tea plant leaf extract, a tea plant flower extract and a tea plant seed extract as active ingredients. The pharmaceutical composition may prevent or improve metabolic syndrome, specifically obesity, hyperlipidemia, hypertension, type 2 diabetes or cardiovascular diseases such as arteriosclerosis, myocardial infarction or angina.

A pharmaceutical composition according to an embodiment of the present disclosure may be administered, for example, orally, rectally, topically, transdermally, intravenously, intramuscularly, intraabdominally or subcutaneously.

Formulations for oral administration include tablet, pill, hard and soft capsule, granule, powder, dust, liquid, emulsion or pellet, but are not limited thereto. These formulations may comprise a diluent (e.g. lactose, dextrose, sucrose, mannitol, sorbitol, cellulose or glycine), a lubricant (e.g. silica, talc, stea plantric acid or polyethylene glycol) or a binder (e.g. magnesium aluminum silicate, starch paste, gelatin, tragacanth, methyl cellulose, sodium carboxymethyl cellulose or polyvinylpyrrolidone), in addition to the active ingredients. As occasion demands, they may also comprise a pharmaceutical additive such as a disintegrant, an absorbent, a colorant, a flavor, a sweetener, etc. A tablet may be prepared by the common mixing, granulation or coating method.

Formulations for parenteral administration include injection, medicinal drop, lotion, ointment, gel, cream, suspension, emulsion, suppository, patch or spray, but are not limited thereto.

The administration dosage of the active ingredients will vary depending on the age, gender and body weight of the subject, pathological conditions to be treated and severity thereof, administration route and discretion of a diagnoser. Determination of the administration dosage considering these factors is in the level of those skilled in the art. A daily dosage may be, for example, 0.1-100 mg/kg/day, more specifically 5-50 mg/kg/day, but is not limited thereto.

In another aspect, the present disclosure provides a food composition comprising a tea plant leaf extract, a tea plant flower extract and a tea plant seed extract as active ingredients. The food composition may prevent or improve metabolic syndrome, specifically obesity, hyperlipidemia, hypertension, type 2 diabetes or cardiovascular diseases such as arteriosclerosis, myocardial infarction or angina. The food composition includes a fancy food or health food composition.

Formulations of the food composition include, for example, tablet, granule, powder, liquid such as drink, gel, bar, etc., but are not particularly limited thereto. The food composition may be prepared by those skilled in the art without difficulty using the active ingredients and other ingredients commonly used in the art considering particular formulation type or purpose of use. A synergic effect may be achieved when the active ingredients are used in combination with other ingredients.

Determination of the administration dosage is in the level of those skilled in the art. A daily dosage may be, for example, 0.1-5000 mg/kg/day, more specifically 50-500 mg/kg/day, but is not limited thereto and may vary depending on various factors such as the age and health condition of the subject, presence of complication(s), or the like.

In another aspect, the present disclosure provides a cosmetic composition comprising a tea plant leaf extract, a tea plant flower extract and a tea plant seed extract as active ingredients. The cosmetic composition may prevent or improve metabolic syndrome, specifically obesity. The cosmetic composition according to the present disclosure may be provided as any topically applicable formulation. For example, it may be provided in the form of oil-in-water emulsion, water-in-oil emulsion, suspension, solid, gel, powder, paste, foam or aerosol. These formulations may be prepared according to a method commonly employed in the art.

The cosmetic composition according to the present disclosure may further comprise a humectant, an emollient, a surfactant, a UV absorbent, an antiseptic, a sterilizer, an antioxidant, a pH adjuster, an organic or inorganic pigment, a fragrance, a cooling agent or an antiperspirant. The amount of these ingredients may be easily determined by those skilled in the art within the range not negatively affecting the purpose and effect of the present disclosure. The content may be 0.01-5 wt %, specifically 0.01-3 wt %, based on the total weight of the composition.

Hereinafter, the present disclosure will be described in further detail through preparation examples, examples and test examples. However, the examples, examples and test examples are provided for illustrative purposes only and not intended to limit the scope of the present disclosure.

Preparation Example 1

Preparation of Tea Plant Leaf Extract

High-quality tea plant leaves were selected and extracted in an extraction vessel at 70-90° C. for 1-2 hours after adding purified water. The resulting solution was separated, filtered and stirred for 30-60 minutes after adding activated clay and activated carbon. After filtering through filter paper, the filtrate was concentrated. After stirring while slowly adding 95% ethanol and allowing to settle, the solution was filtered again through filter paper, concentrated, sterilized and spray dried. A tea plant extract comprising 200 mg/g or more catechin was obtained.

Preparation Example 2

Preparation of Tea Plant Flower Extract

Tea plant flower was washed by adding water, filtered, pulverized to make extraction easier, and extracted while stirring after adding hot (60-70° C.) water. The resulting solution was separated into solid and liquid components using a compression filter. The liquid component was concentrated under reduced pressure, homogenized by mixing with maltodextrin and spray dried.

Preparation Example 3

Preparation of Tea Plant Seed Extract

A tea plant seed extract was prepared in substantially the same manner as Preparation Example 2 using the seed of tea plant.

EXAMPLES

The tea plant leaf extract, the tea plant flower extract and the tea plant seed extract prepared above were mixed at a ratio of 9:0.5:0.5 (Example 1) or 6:2:2 (Example 2).

Test Example 1

Activation of AMPK by Tea Plant Leaf Extract, Tea Plant Flower Extract, Tea Plant Seed Extract and Mixture Thereof Activation of AMPK, which is involved in insulin resistance that is the main cause of metabolic syndrome, in hepatocytes by the tea plant leaf extract, the tea plant flower extract, the tea plant seed extract and the mixture of the extracts was investigated.

Human hepatocytes (Zen-Bio, Research Triangle Park, N.C., USA) were cultured using a medium for hepatocytes (HM-2, Zen-Bio) in a 5% $CO_2$ incubator at 37° C. The cultured cells were treated with the tea plant leaf extract, the tea plant flower extract, the tea plant seed extract or the mixture of the extracts dissolved in DMSO (10 µM) for 24 hours. DMSO of 1/1000 of the volume of the medium was used as negative control and 1 mL of AICAR (Cell Signaling Technology, Inc. UK) known as AMPK activator was used as positive control. 24 hours later, the cells were washed twice with cold PBS and protein was isolated using RIPA buffer (Santa Cruz Biotechnology, Santa Cruz, Calif., USA). The isolated protein was quantitated with a BCA assay kit (Pierce, Rockford, USA) and 30 µg was subjected to western blotting using the iBlot Dry blotting system (Invitrogen, Carlsbad, Calif., USA). AMPK activation was measured using anti-AMPK-α (cell signaling) and anti-phospho-AMPK-α (cell signaling) antibodies. The result is shown in FIG. 1.

As seen from FIG. 1, the mixture of the tea plant leaf extract, the tea plant flower extract and the tea plant seed extract exhibited better AMPK activating effect than when the hepatocytes were treated with the extracts alone and the effect was comparable to that of the positive control AICAR. That is to say, the mixture of the tea plant leaf extract, the tea plant flower extract and the tea plant seed extract provide a synergic effect of activating AMPK and preventing or improving metabolic syndrome as compared to when the extracts are used alone.

Test Example 2

Influence of Weight Ratio of Tea Plant Flower Extract and Tea Plant Seed Extract in Mixture on AMPK Activating Effect To determine an optimal weight ratio of a tea plant flower extract and a tea plant seed extract in a mixture of a tea plant leaf extract, a tea plant flower extract and a tea plant seed extract, mixture samples containing 5%, 10%, 20%, 40% and 80% by weight of the tea plant flower extract and the tea plant seed extract were prepared and dissolved in DMSO to a concentration of 10 µM. Hepatocytes cultured in substantially the same manner as Test Example 1 were treated with the samples for 24 hours. Then, AMPK activating effect was evaluated by western blotting in substantially the same manner as Test Example 1. The result is shown in FIG. 2.

Figure 2:
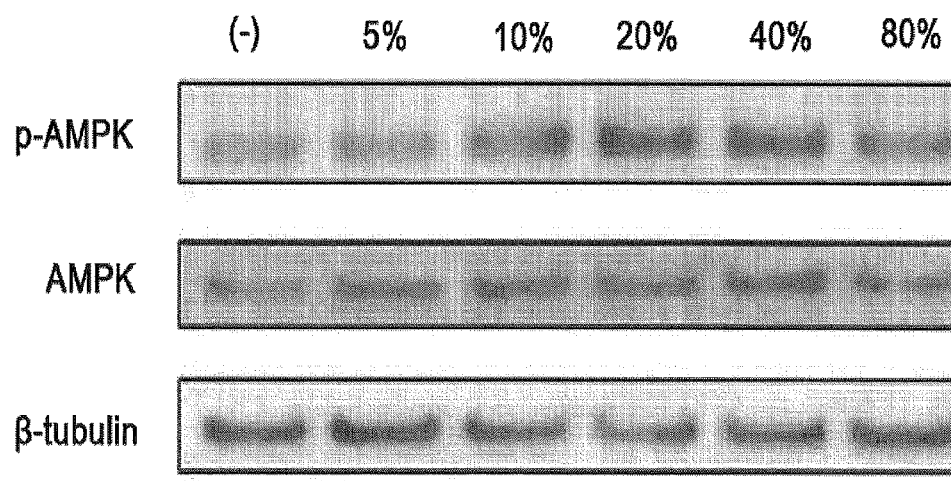
FIG. 2 shows change in AMPK activity after treating hepatocytes with a mixture of a tea plant leaf extract, a tea plant flower extract and a tea plant seed extract with different wt % of the tea plant flower extract and the tea plant seed extract.

As seen from FIG. 2, the AMPK activating effect was high when the content of the tea plant flower extract and the tea plant seed extract in the mixture was in the range from 10 to 40 wt %. In particular, within the range where the content of the tea plant flower extract and the tea plant seed extract in the mixture was from 10 to 40%, the AMPK activating effect increased as the content of the two extracts was higher. Based on this result, in the following experiments using mixtures of a tea plant leaf extract, a tea plant flower extract and a tea plant seed extract, mixtures in which the content of the tea plant flower extract and the tea plant seed extract is 10 wt % (Example 1) and 40 wt % (Example 2) were used.

Test Example 3

Activation of AMPK in Metabolic Cells by Mixture of Tea Plant Leaf Extract, Tea Plant Flower Extract and Tea Plant Seed Extract AMPK activating effect of a mixture of a tea plant leaf extract, a tea plant flower extract and a tea plant seed extract was evaluated using adipocytes, hepatocytes and myocytes involved in energy metabolism. Human adipocytes, hepatocytes and myocytes were acquired from Zen-Bio (Research Triangle Park, N.C., USA) and cultured using a medium for adipocytes (OM-AM, Zen-Bio), a medium for hepatocytes (HM-2, Zen-Bio) and a medium for myocytes (SKM-D, SKM-M, Zen-Bio), respectively, in a 5% $CO_2$ incubator at 37° C. The respective cells were treated for 24 hours with the extract of Example 1 or Example 2 dissolved in DMSO to a concentration of 10 µM. DMSO was used as negative control and AICAR was used as positive control. AMPK activating effect was evaluated by western blotting in substantially the same manner as Test Example 1. The result is shown in FIG. 3.

Figure 3:
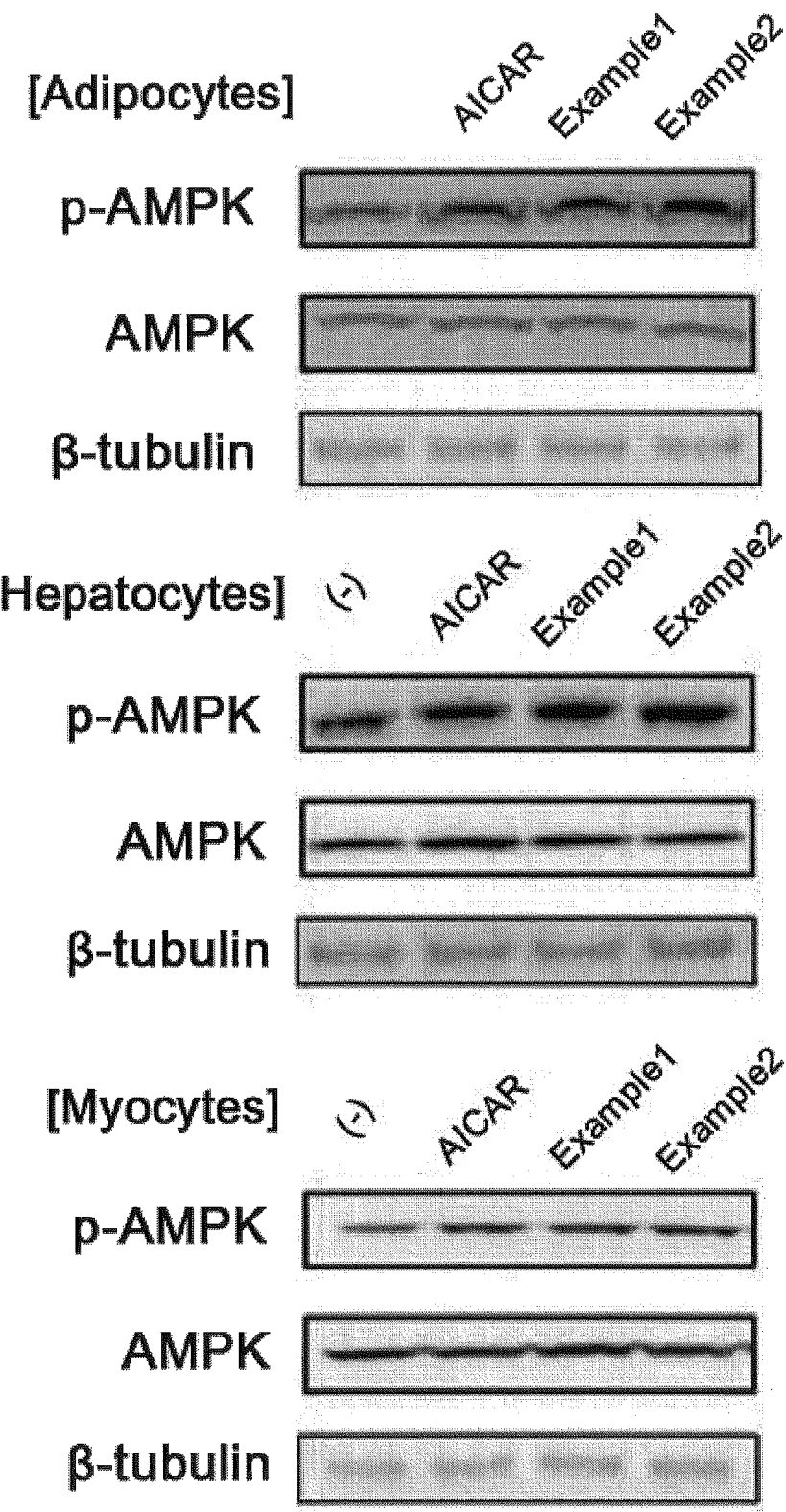
FIG. 3 shows change in AMPK activity after treating adipocytes, hepatocytes and myocytes with a mixture of a tea plant leaf extract, a tea plant flower extract and a tea plant seed extract.

As seen from FIG. 3, the mixture of a tea plant leaf extract, a tea plant flower extract and a tea plant seed extract exhibited strong AMPK activating effect in all of the adipocytes, hepatocytes and myocytes involved in metabolism. In particular, the mixture of Example 2 in which the content of the tea plant flower extract and the tea plant seed extract was 40% exhibited higher AMPK activity in all of the adipocytes, hepatocytes and myocytes as compared to that of Example 1 in which the content of the tea plant flower extract and the tea plant seed extract was 10%.

Test Example 4

Figure 5:
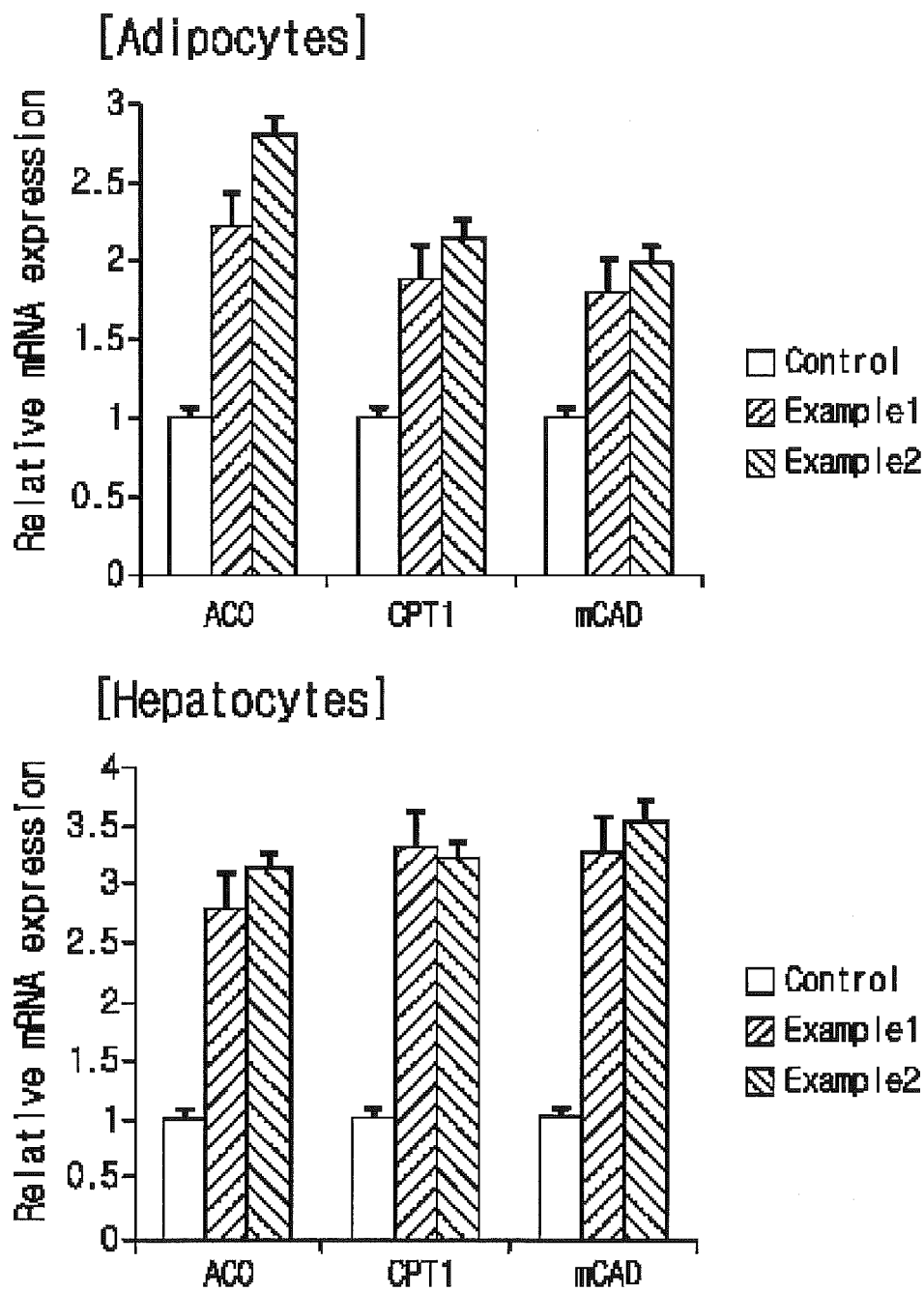
FIG. 5 shows increased expression of fatty acid oxidation-related genes in adipocytes and hepatocytes treated with a mixture of a tea plant leaf extract, a tea plant flower extract and a tea plant seed extract.

Regulation of Expression of Fat Metabolism-Related Genes by Mixture of Tea Plant Leaf Extract, Tea Plant Flower Extract and Tea Plant Seed Extract Human adipocytes and hepatocytes were treated with the mixture of a tea plant leaf extract, a tea plant flower extract and a tea plant seed extract of Example 1 or Example 2 in substantially the same manner as Test Example 3. After washing twice with cold PBS, the cells were treated with TRIzol reagent (Invitrogen) to extract RNA and cDNA was synthesized using the RevertAid First Strand cDNA synthesis kit (Fermentas). Change in expression of the fatty acid synthesis-related genes SREBP-1c (sterol regulatory element-binding protein-1c), ACC (acetyl-CoA carboxylase) and FAS (fatty acid synthase) and the fatty acid oxidation-related genes ACO (acyl-CoA oxidase), CPT1 (carnitine palmitoyltransferase 1) and mCAD (medium-chain acyl-CoA dehydrogenase) was investigated. PCR and analysis were performed using the Rotor-Gene 3000 system (Corbett Research, Sydney, Australia). The result is shown in FIG. 4 and FIG. 5.

As seen from the figures, treatment with the mixture of a tea plant leaf extract, a tea plant flower extract and a tea plant seed extract inhibited the expression of the fatty acid synthesis-inducing genes (FIG. 4) and, at the same time, increased the expression of the fatty acid oxidation-facilitating genes (FIG. 5) both in the adipocytes and hepatocytes. The effect of inhibiting expression of the fatty acid synthesis-inducing genes and increasing expression of the fatty acid oxidation-facilitating genes was higher in Example 2, in which the content of the tea plant flower extract and the tea plant seed extract was higher, than in Example 1. From this result, it can be seen that the mixture of a tea plant leaf extract, a tea plant flower extract and a tea plant seed extract inhibits fatty acid synthesis and, at the same time, facilitates fatty acid oxidation and this effect is higher as the content of the tea plant flower extract and the tea plant seed extract is higher.

Test Example 5

Facilitation of Fatty Acid Oxidation by Mixture of Tea Plant Leaf Extract, Tea Plant Flower Extract and Tea Plant Seed Extract Human adipocytes, hepatocytes and myocytes were treated with the mixture of Example 1 or Example 2 in substantially the same manner as Test Example 1 and fatty acid (palmitate) oxidation was measured. The respective cells were cultured on a 12-well culture dish and incubated in a 5% $CO_2$ incubator at 37° C. for 3 hours after adding 490 μL of serum-free medium and 10 μL of substrate ([9,10$^{-3}$H] palmitic acid, 0.2 μCi, final concentration=5 μmol/L). 100 μL of the cell culture was passed through an ion-exchange column and 750 μL of distilled water was flown twice. The liquid (HO$^3$H) that passed through the ion-exchange column was collected and the quantity of the radioactive isotope $^3$H was measured using a liquid scintillation spectrophotometer. The result is shown in FIG. 6.

Figure 6:
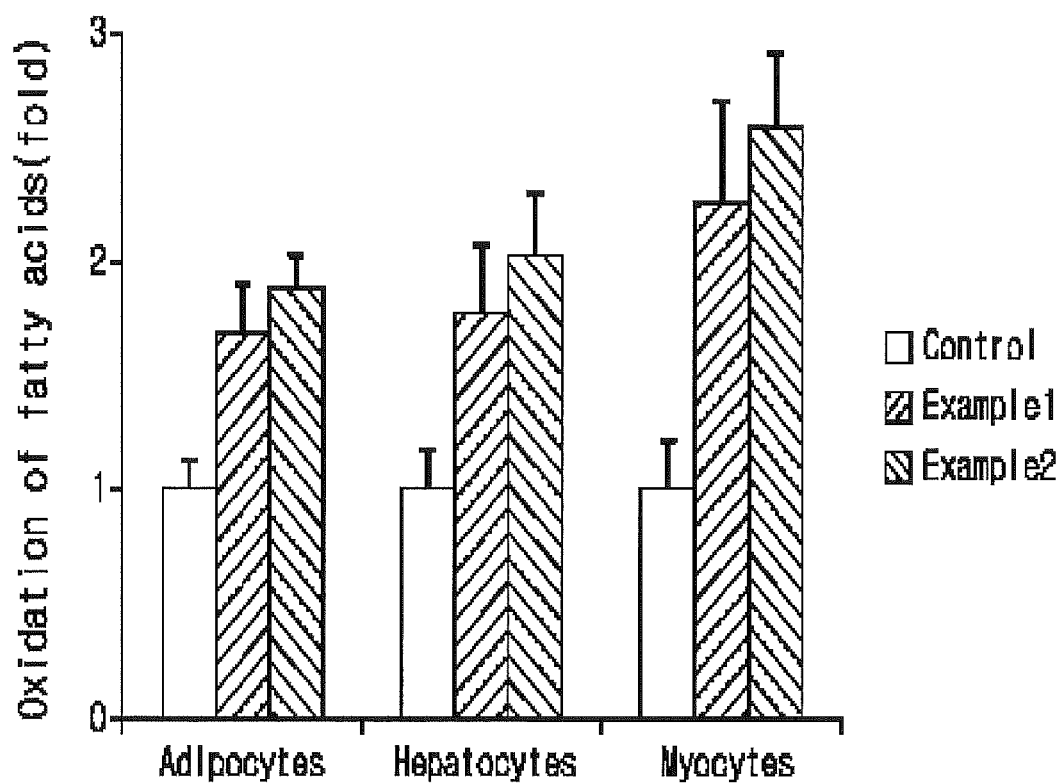
FIG. 6 shows increased oxidation of fatty acids in adipocytes, hepatocytes and myocytes treated with a mixture of a tea plant leaf extract, a tea plant flower extract and a tea plant seed extract.

As seen from FIG. 6, fatty acid oxidation was promoted when the cells were treated with the mixtures of a tea plant leaf extract, a tea plant flower extract and a tea plant seed extract of Example 1 and Example 2. In particular, the fatty acid oxidation promoting effect was superior in Example 2 in which the content of the tea plant flower extract and the tea plant seed extract was higher. From this result, it can be seen that the mixture of a tea plant leaf extract, a tea plant flower extract and a tea plant seed extract has a superior effect of facilitating fatty acid oxidation.

Test Example 6

Enhancement of Glucose Uptake by Mixture of Tea Plant Leaf Extract, Tea Plant Flower Extract and Tea Plant Seed Extract Human adipocytes and hepatocytes were seeded on a 24-well culture dish with no empty space and were treated with the mixture of Example 1 or Example 2 in substantially the same manner as Test Example 1. After one day, the cells were washed with PBS and incubated in a 5% $CO_2$ incubator at 37° C. for at least 12 hours after adding DMEM medium containing 1% BSA and low-concentration glucose. After incubation in HEPES solution for 30 minutes at 37° C., 1 μCi/mL of [$^{14}$C]2-deoxyglucose and 1 mM glucose were added. After further incubation at 22° C. for 30 minutes, the quantity of $^{14}$C that migrated into the cells was measured to investigate glucose uptake. The result is shown in FIG. 7.

Figure 7:
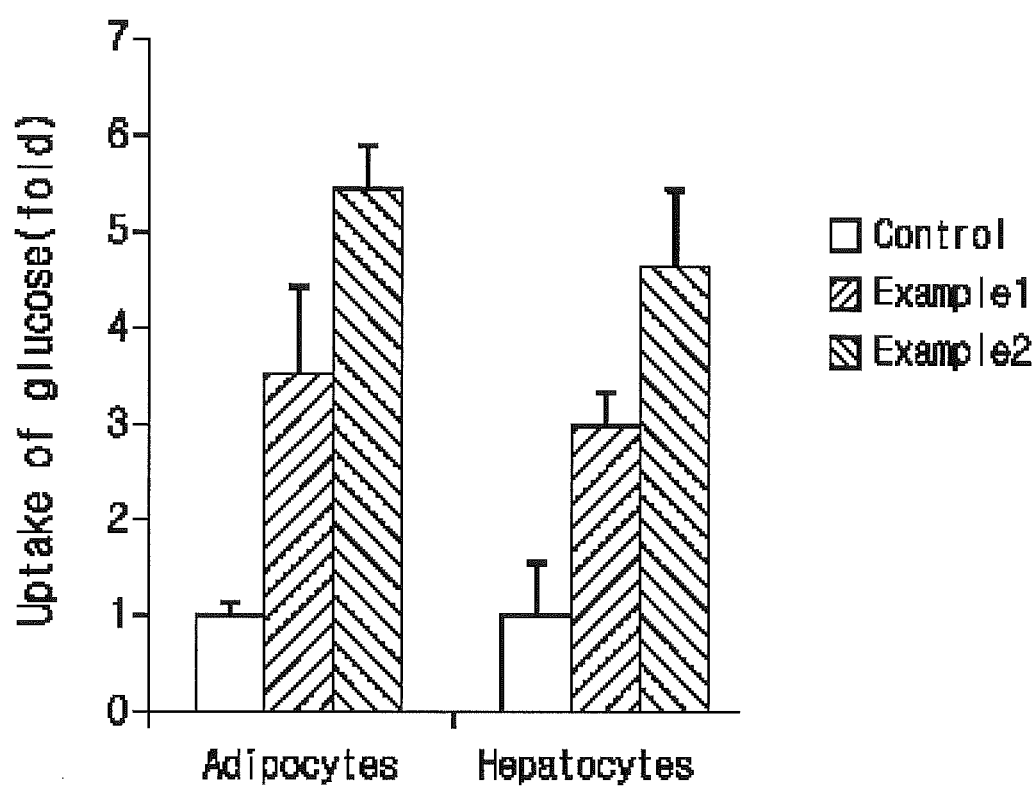
FIG. 7 shows increased uptake of glucose in human adipocytes and hepatocytes treated with a mixture of a tea plant leaf extract, a tea plant flower extract and a tea plant seed extract.

As seen from FIG. 7, treatment with the mixtures of a tea plant leaf extract, a tea plant flower extract and a tea plant seed extract of Example 1 and Example 2 resulted in increased glucose uptake and insulin sensitivity in the human adipocytes and hepatocytes. This effect was superior in Example 2 in which the content of the tea plant flower extract and the tea plant seed extract was higher. From this result, it can be seen that the mixture of a tea plant leaf extract, a tea plant flower extract and a tea plant seed extract can prevent or improve glucose metabolic syndrome by increasing insulin sensitivity.

Formulation examples of the composition according to the present disclosure are described below. However, other formulations are also possible and the following examples are provided for illustrative purposes only and not intended to limit the scope of the present disclosure.

Formulation Example 1

Health Food

| | |
|---|---|
| Mixture of tea leaf extract, tea flower extract and tea seed extract | 1000 mg |
| Vitamin mixture | |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

The described contents of the vitamin and mineral mixtures are given as appropriate examples for health food, but they may be changed in compositions or contents.

Formulation Example 2

Health Drink

| | |
|---|---|
| Mixture of tea leaf extract, tea flower extract and tea seed extract | 1000 mg |
| Citric acid | 1000 mg |
| Oligosaccharide | 100 g |
| Taurine | 1 g |
| Purified water | Balance |

According to the commonly employed health drink preparation method, the above ingredients are mixed and heated for about 1 hour at 80-90° C. with stirring. The resulting solution is filtered and sterilized.

Formulation Example 3

Tablet 100 mg of mixture of tea leaf extract, tea flower extract and tea seed extract are mixed with 50 mg of soybean extract, 100 mg of glucose, 50 mg of red ginseng extract, 96 mg of starch and 4 mg of magnesium stea plantrate. After granulation by adding 40 mg of 30% ethanol, followed by drying at 50-60° C., the granule is prepared into tablet.

Formulation Example 4

Granule 100 mg of mixture of tea leaf extract, tea flower extract and tea seed extract are mixed with 50 mg of soybean extract, 100 mg of glucose and 600 mg of starch. After granulation by adding 100 mg of 30% ethanol, the granule is dried at 60° C.

Formulation Example 5

Cream

Cream is prepared according to the commonly employed method using the ingredients described in Table 1.

TABLE 1

| Ingredients | Contents (wt %) |
|---|---|
| Mixture of tea leaf extract, tea flower extract and tea seed extract | 3.0 |
| Polyethylene glycol monostea plantrate | 2.0 |
| Glycerin monostea plantrate | 5.0 |
| Cetyl alcohol | 4.0 |
| Squalene | 3.0 |
| Glyceryl tri-2-ethylhexanoate | 6.0 |
| Sphingolipid | 1.0 |
| 1,3-Butylene glycol | 7.0 |
| Purified water | Balance |

While the exemplary embodiments have been shown and described, it will be understood by those skilled in the art that various changes in form and details may be made thereto without departing from the spirit and scope of the present disclosure as defined by the appended claims.

What is claimed is:

1. A method for inhibiting or improving metabolic syndrome, comprising administering an effective amount of a combination of a tea plant leaf extract, a tea plant flower extract and a tea plant seed extract to a subject in such need, wherein a weight ratio of the tea plant leaf extract and the tea plant flower extract plus the tea plant seed extract in the combination is 6-9:0.5-4.

2. The method according to claim 1, wherein a weight ratio of the tea plant leaf extract, the tea plant flower extract and the tea plant seed extract in the combination is 6-9:0.5-2:0.5-2.

3. The method according to claim 1, wherein the metabolic syndrome comprises at least three of abdominal obesity, high cholesterol, hypertension, and high blood sugar.

4. The method according to claim 1, wherein the combination is administered in a form of a composition, wherein the composition comprises the combination in an amount of 1-80 wt % based on the total weight of the composition.

* * * * *